(12) United States Patent
Kelker et al.

(10) Patent No.: US 9,534,218 B2
(45) Date of Patent: Jan. 3, 2017

(54) EXPRESSION OF MAIZE CODON OPTIMIZED PROTEINS IN PSEUDOMONAS FLUORESCENS

(71) Applicant: Dow AgroSciences LLC, Indianapolis, IN (US)

(72) Inventors: Matthew Kelker, Zionsville, IN (US); Aaron T. Woosley, Fishers, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/409,416

(22) PCT Filed: Jun. 13, 2013

(86) PCT No.: PCT/US2013/045548
§ 371 (c)(1),
(2) Date: Dec. 18, 2014

(87) PCT Pub. No.: WO2013/191997
PCT Pub. Date: Dec. 27, 2013

(65) Prior Publication Data
US 2015/0191721 A1    Jul. 9, 2015

Related U.S. Application Data

(60) Provisional application No. 61/660,974, filed on Jun. 18, 2012.

(51) Int. Cl.
| | |
|---|---|
| *C12N 15/64* | (2006.01) |
| *C12N 15/11* | (2006.01) |
| *C12N 15/63* | (2006.01) |
| *C12N 15/78* | (2006.01) |
| *C12P 21/00* | (2006.01) |
| *C12N 1/21* | (2006.01) |
| *C12N 15/67* | (2006.01) |

(52) U.S. Cl.
CPC ............. *C12N 15/11* (2013.01); *C12N 15/63* (2013.01); *C12N 15/64* (2013.01); *C12N 15/78* (2013.01); *C12P 21/00* (2013.01); *C12N 2310/353* (2013.01)

(58) Field of Classification Search
None
See application file for complete search history.

(56) References Cited

U.S. PATENT DOCUMENTS

| | | |
|---|---|---|
| 2006/0205653 A1 | 9/2006 | Larrinua et al. |
| 2009/0069229 A1 | 3/2009 | Smith et al. |
| 2016/0075733 A1* | 3/2016 | Bancel ................ A61K 48/005 424/489 |

FOREIGN PATENT DOCUMENTS

| | | |
|---|---|---|
| WO | 2013191997 | 12/2013 |

OTHER PUBLICATIONS

International Search Report; PCT/US2013/045548; dated Nov. 15, 2013; 3 pgs.

Madduri et al., Expression of phosphinothricin N-acetyltransferase in *Escherichia coli* and *Pseudomonas fluorescens*: Influence of mRNA secondary structure, host, and other physiological conditions; ScienceDirect; Protein Expression and Purification 55 (2007) 352-360.

* cited by examiner

*Primary Examiner* — Nancy J Leith
(74) *Attorney, Agent, or Firm* — Ronald S. Maciak; Magleby Cataxinos & Greenwood

(57) ABSTRACT

Compositions and methods for improving expression of a recombinant protein or polypeptide of interest in a host cell are provided. Compositions comprising a polynucleotide coding sequence for a BTBooster are provided using a plant optimized system. The coding sequences can be used in vector constructs or expression systems for transformation and expression of a recombinant protein or polypeptide of interest in a host cell. Methods comprising the codon optimization of a polynucleotide coding sequence for increased expression in a bacterial host are provided. The codon optimization method can be used in designing a polynucleotide coding sequence which expresses robust levels of protein in a bacterial host cell.

12 Claims, No Drawings

```
                         SEQUENCE LISTING

<160> NUMBER OF SEQ ID NOS: 5

<210> SEQ ID NO 1
<211> LENGTH: 319
<212> TYPE: PRT
<213> ORGANISM: Bacillus thuringiensis

<400> SEQUENCE: 1

Met His Leu Glu Cys Ile Ser Ala Thr Asp Pro Asp Gly Leu His Ala
1               5                   10                  15

Gly Val Val Thr Phe Gln Val Val Gly Asp Glu Glu Ser Gln Ala Tyr
            20                  25                  30

Phe Gln Val Val Asn Asp Gly Ala Asn Leu Gly Ser Leu Ser Leu Leu
        35                  40                  45

Gln Ala Val Pro Glu Glu Ile Ala Glu Phe Ser Ile Thr Ile Cys Ala
    50                  55                  60

Thr Asp Gln Gly Thr Asp Pro Gly Pro Leu Ser Thr Asp Met Thr Phe
65                  70                  75                  80

Ala Val Val Phe Val Pro Thr Gln Gly Glu Pro Ala Phe Ala Ser Ser
                85                  90                  95

Glu His Ala Val Ala Phe Ile Glu Ala Ser Ala Gly Met Glu Glu Ser
            100                 105                 110

His Gln Leu Pro Leu Ala Gln Asp Ile Ala Asn His Leu Cys Glu Asp
        115                 120                 125
```

```
Asp Cys His Ser Ile Tyr Tyr Ala Ile Ile Asp Gly Asn Ser Glu Gly
            130                 135                 140

His Phe Gly Leu Asp Pro Val Ala Asn Ala Leu Phe Leu Ser Ala Glu
145                 150                 155                 160

Leu Ile Ala Glu Gln Ser Ala Ser His Thr Leu Gln Val Ala Ala Ser
                165                 170                 175

Asn Ser Pro Asp Gly Gly Ile Pro Leu Pro Ala Ser Ile Leu Thr Val
            180                 185                 190

Thr Val Thr Val Ala Glu Ala Asp Pro Ala Pro Val Phe Met Ala Glu
        195                 200                 205

Leu Tyr Thr Ala Gly Ile Ser Thr Ala Asp Ser Ile Gly Cys Glu Leu
210                 215                 220

Leu Ala Leu His Ala Thr Gln Ser Glu Gly Ala Ala Ile Thr Tyr Ala
225                 230                 235                 240

Ile Asp Tyr Asp Thr Met Val Val Asp Pro Ser Leu Glu Ala Val Cys
                245                 250                 255

Gln Ser Ala Phe Val Leu Asn Ala Gln Thr Gly Val Leu Thr Leu Asn
            260                 265                 270

Ile Gln Pro Thr Ala Thr Met His Gly Leu Phe Asn Phe Glu Val Thr
        275                 280                 285

Ala Thr Asp Thr Ala Gly Ala Gln Asp Arg Thr Asp Val Thr Val Tyr
290                 295                 300

Val Val Ser Ser Gln Asn Arg Leu Glu His His His His His His
305                 310                 315
```

<210> SEQ ID NO 2
<211> LENGTH: 1011
<212> TYPE: DNA
<213> ORGANISM: Artificial Sequence
<220> FEATURE:
<223> OTHER INFORMATION: Codon optimized version of BTB which
      incorporates maize codons

<400> SEQUENCE: 2

```
gcactagtcg ggctagcagg aggtaactta tgcacctcga atgtatcagc gctactgatc    60
cggacggtct ccacgctggg gttgtgacct tccaagtggt cggagacgag gagtcgcaag   120
cctactttca gtcgtcaac gacggtgcta accttggatc attgtcactg ctgcaagccg    180
ttcccgagga gatagcggag tttagcatca ccatctgtgc gaccgatcaa ggcaccgacc    240
ctggtccgct ctctactgac atgacttttg ccgtcgtttt cgtgcccacg caagggaac    300 cagcatttgc ctcgtctgaa catgcagttg ccttcattga ggcttctgct ggcatggaag    360
aatcccacca gctccccttg cacaagata tcgcaaacca cctttgcgag acgattgcc     420 actctatcta ctatgcaatc atagatggca actccgaggg tcactttggg ttggacccag    480
tggcgaacgc tcttttcctt tctgccgagt tgattgcaga gcagtcagcg tcacatacac    540
tccaagtcgc agccagcaat tcaccagatg gaggcatccc tcttccagct cgatcctca    600 cagtgaccgt gacagttgca gaagcggacc cagcacccgt tttcatggca gagctttaca    660
ccgctgggat ttcaacagcc gactccatag gttgcgagct gcttgcattg cacgcaacgc    720
aatcagaagg agctgcgatc acctacgcta tagactacga cactatggtc gtggacccat    780
cgctggaagc ggtctgccag tcagcttttg tcctcaacgc tcagacggga gtgcttacac    840
tcaacatcca acccacagct actatgcacg gactgttcaa cttcgaagtg accgctacgg    900
atacagctgg tgcccaagat agaacggatg tcactgtgta tgtcgtcagc tctcagaata   960
```

```
ggctcgaaca ccatcaccat caccactgat aatagctcga ggtcgaccac g        1011
```

<210> SEQ ID NO 3
<211> LENGTH: 957
<212> TYPE: DNA
<213> ORGANISM: Artificial Sequence
<220> FEATURE:
<223> OTHER INFORMATION: Codon optimized version of BTB which
      incorporates Escherichia coli codons

<400> SEQUENCE: 3

```
atgcacctgg aatgtatctc tgcaaccgac ccggatggcc tgcatgctgg tgtagtaact    60
ttccaagtgg ttggtgacga agaaagccag gcttatttcc aggttgttaa cgacggtgca   120
aacctgggct cccttccct gctgcaggcc gtgccagaag aaatcgcaga gttcagcatt    180
accatctgcg ctaccgacca agtaccgac ccgggcccgc tgagcaccga catgaccttc    240
gctgttgtat tcgttcctac tcagggtgaa ccagctttcg cttcctctga gcacgcagta   300
gcattcatcg aagcctccgc gggtatgaa gaatctcatc agctcccact ggctcaagat    360
atcgcgaacc atctgtgtga agacgactgc cactctatct actacgctat catcgacggt   420
aacagcgaag tcacttcgg tctggacccg gtagctaacg cgctgttcct gtctgctgaa    480
ctgatcgcgg aacagagcgc ttctcacact ttacaagttg ctgcgtccaa cagcccggac   540
ggtggcatcc ctctgcctgc atctatcctt accgttaccg taaccgtcgc tgaagcagat   600
ccagcaccgg tattcatggc tgagctgtac acggctggca tcagcactgc cgactccatt   660
ggctgcgaac ttctggctct gcatgcgact cagtcagaag gcgcggccat cacctatgct   720
atcgactatg ataccatggt agttgatccg tctctggaag cagtttgcca gtctgctttc   780
gttctgaacg cacagactgg tgttctgact ctgaacatcc agccgactgc aacgatgcat   840
ggtctgttca acttcgaagt tactgcgacc gacactgcgg gcgctcagga ccgtactgac   900
gttaccgtct acgtagtgtc ttctcagaac cgtctggaac accaccaca ccaccac      957
```

<210> SEQ ID NO 4
<211> LENGTH: 63
<212> TYPE: DNA
<213> ORGANISM: Artificial Sequence
<220> FEATURE:
<223> OTHER INFORMATION: Forward primer

<400> SEQUENCE: 4

```
gcactagtcg ggctagcagg aggtaactta tgcacctgga atgtatctct gcaaccgacc    60
cgg                                                                 63
```

<210> SEQ ID NO 5
<211> LENGTH: 78
<212> TYPE: DNA
<213> ORGANISM: Artificial Sequence
<220> FEATURE:
<223> OTHER INFORMATION: Reverser primer sequence

<400> SEQUENCE: 5

```
cgtggtcgac ctcgagctat tatcagtggt ggtggtggtg gtgttccaga cggttctgag    60
aagacactac gtagacgg                                                 78
```

US 9,534,218 B2

EXPRESSION OF MAIZE CODON OPTIMIZED PROTEINS IN PSEUDOMONAS FLUORESCENS

CROSS-REFERENCE TO RELATED APPLICATIONS

This application claims the benefit of U.S. Provisional Application 61/660,974 filed on Jun. 18, 2012, which is expressly incorporated by reference herein.

REFERENCE TO SEQUENCE LISTING SUBMITTED ELECTRONICALLY

The official copy of the sequence listing is submitted electronically via EFS-Web as an ASCII formatted sequence listing with a file named "70010 Sequence Listing", created on Jun. 1, 2012, and having a size of 6,505 bytes and is filed concurrently with the specification. The sequence listing contained in this ASCII formatted document is part of the specification and is herein incorporated by reference in its entirety.

FIELD OF THE INVENTION

This disclosure applies to the technical field of molecular genetics wherein a polynucleotide sequence which encodes a gene is codon optimized for the production of heterologous proteins in *Pseudomonas fluorescens*. In addition, the present disclosure provides increased recombinant protein production in host cells through the improved expression.

BACKGROUND

Recombinant proteins are produced and marketed in numerous agricultural, industrial and pharmaceutical applications. The robust productions of large quantities of recombinant proteins are necessary to provide abundant amounts of protein for these commercial applications. Unlike small molecules which are efficiently produced through chemical synthesis, the production of proteins and polypeptides are most efficiently produced in living cells such as bacteria, plants, or mammalian cells.

The *Pseudomonas fluorescens* expression system has been developed for efficiently producing large quantities of recombinant proteins. This expression system provides significant advantages for the expression of heterologous genes as compared to other known cellular expression systems. The quality, stability, solubility, titer, and rapid delivery of recombinant proteins produced by the *Pseudomonas fluorescens* expression system are superior to other know cellular expression systems. Moreover, the *Pseudomonas fluorescens* expression system is used to express proteins that cannot be expressed in other systems. As such, the *Pseudomonas fluorescens* expression system is a preferred system for the efficient production of recombinant proteins, thereby resulting in reduced costs for the production and development of recombinant proteins.

Improvements to the *Pseudomonas fluorescens* expression system have been developed to refine the system for the production of recombinant proteins via the heterologous expression of genes. US Pat App No. 2005/0186666 describes an improved expression system for the production of recombinant polypeptides utilizing auxotrophic selectable markers. US Pat App No. 2006/0008877 describes an improved method for producing recombinant proteins using Sec-system secretion signal peptides for secretion of recombinant proteins and peptides. US Pat App No. 2005/0202544 and International Pat App No. 2006/133210 describe novel inducible-promoters for commercial *Pseudomonas fluorescens* fermentation systems. US Pat App No. 2006/0110747 describes a process for improving the production levels of recombinant proteins by comparing two genetic profiles of a cell that expresses a recombinant protein and modifying the cell to change the expression of a gene product that is upregulated in response to the recombinant protein expression. US Pat App No. 2009/0162898 describes improved copy number plasmids containing a deletion, insertion, or substitution in the replication control region. US Pat App No. 2009/0062143 describes ribosomal binding site sequences for optimal expression of a heterologous protein. Despite the development of these innovations to the *Pseudomonas fluorescens* expression system, there is still a need in the art for improvements which result in the production of large quantities of recombinant proteins by the expression of heterologous genes.

The subject disclosure provides a novel method for the codon optimization of a polynucleotide sequence which results in robust production of large quantities of recombinant proteins via the *Pseudomonas fluorescens* expression system.

BRIEF SUMMARY OF THE INVENTION

The subject disclosure concerns a method for optimizing a polynucleotide sequence for increased levels of recombinant protein expression in a bacterial host cell. The increased levels of expression of the protein were the result of using the codon optimization method of the subject disclosure. A preferred embodiment utilizes plant preferred codons within the coding sequence of the polynucleotide sequence which is codon optimized using the codon optimization method of the subject disclosure. A more preferred embodiment utilizes *Zea mays* preferred codons within the coding sequence of the polynucleotide sequence which is codon optimized using the codon optimization method of the subject disclosure.

An embodiment of the disclosure includes a bacterial host cell consisting of a *Pseudomonas* cell, an *Escherichia* cell, an *Acidovorax* cell, an *Brevundimonas* cell, an *Burkholderia* cell, an *Hydrogenophaga* cell, an *Oceanimonas* cell, an *Ralstonia* cell, an *Stenotrophomonas* cell, an *Sphingomonas* cell, an *Xanthomonas* cell, or an *Acidomonas* cell. An especially preferred embodiment of the subject disclosure includes a bacterial host cell consisting of *Pseudomonas fluorescens*.

An embodiment of the disclosure includes codon optimization design modifications, such as the removal of polynucleotide sequences which can affect transcription or translation of the gene of interest. These polynucleotide sequences include stem loop structures, exon:intron junctions (5' or 3'), poly A addition signals, or RNA polymerase termination signals. These polynucleotide sequences are identified and removed by the substitution of maize preferred codons.

Another embodiment of the disclosure includes the removal and reduction of TA or CG doublets. In addition to the doublets, [G+C] or [A+1] sequence blocks that have more than about six residues are removed as these sequences can affect transcription or translation of the sequence. These polynucleotide sequences are identified and removed by the substitution of maize preferred codons.

An embodiment of the disclosure includes the removal of stable intrastrand secondary structures from the polynucleotide sequence. Stem loop structures that can spontaneously form within a mRNA polynucleotide sequence are known in the art to hinder translation of a recombinant protein. These polynucleotide sequences are identified and removed by the substitution of maize preferred codons.

An embodiment of the disclosure includes the removal of restriction enzyme binding sequences from the polynucleotide sequence. Superfluous restriction enzyme binding sites within a polynucleotide sequence can encumber cloning strategies for the completion of DNA constructs. These polynucleotide sequences are identified and removed by the substitution of maize preferred codons.

An embodiment of the disclosure includes an isolated polynucleotide sequence of the BTB gene. This coding sequence is codon optimized to contain maize preferred codons. In addition, the sequence has been designed to remove superfluous restriction enzyme sites, to remove stable intrastrand secondary structures, to remove TA and CG doublets, to remove [G+C] or [A+1] sequence blocks, and to remove polynucleotide sequences which can affect transcription or translation.

An embodiment of the disclosure includes a DNA construct containing the codon optimized BTB polynucleotide sequence. The DNA construct is transformed into a *Pseudomonas fluorescens* host cell and recombinant protein is produced from the *Pseudomonas fluorescens* host cell via a fermentation process. The recombinant protein can be subsequently isolated and purified.

An embodiment of the disclosure includes codon optimizing the BTB polynucleotide coding sequence using the codon optimization method of the subject disclosure. The resulting codon optimization results in an increase in recombinant protein expression. The increase in recombinant protein concentration is from 1×, 2.5×, 5×, 10×, 15×, 20×, 30×, or 40× the level of protein concentration of a BTB polynucleotide sequence that has not been codon optimized using the codon optimization method of the subject disclosure.

BRIEF DESCRIPTION OF THE SEQUENCES

SEQ ID NO:1 lists the BTB protein sequence.

SEQ ID NO:2 lists the *Zea mays* (maize) optimized version of the BTB polynucleotide sequence.

SEQ ID NO:3 lists the *Escherichia coli* optimized version of the BTB polynucleotide sequence.

SEQ ID NO:4 lists the forward primer used to PCR amplify SEQ ID NO:3.

SEQ ID NO:5 lists the reverse primer used to PCR amplify SEQ ID NO:3.

DETAILED DESCRIPTION OF THE INVENTION

Compositions and methods for producing large quantities and high levels of polypeptides in a host cell are provided. In particular, a novel codon optimization method is described which results in a polynucleotide sequence that is expressed at higher levels and in larger quantities via a fermentation system. The novel codon optimization method of the subject disclosure provides an unexpected improvement for designing a polynucleotide sequence, wherein higher levels and greater quantities of recombinant protein are expressed using the *Pseudomonas fluorescens* expression system.

The term "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). As a result, many amino acids are designated by more than one codon. For example, the amino acids alanine and proline are coded for by four triplets, serine and arginine by six triplets, whereas tryptophan and methionine are coded by just one triplet. This degeneracy allows for DNA base composition to vary over a wide range without altering the amino acid sequence of the proteins encoded by the DNA. The "genetic code" which defines the codons that encode specific amino acids is well known in the art.

Many organisms display a bias for use of particular codons to code for the insertion of a particular amino acid in a growing peptide chain. Codon preference, or codon bias, and the resulting differences in codon usage between organisms is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at www.kazusa.or.jp/codon/ and these tables can be adapted in a number of ways. See Nakamura et al. *Nucl. Acids Res.* 28:292 (2000). By utilizing this or similar tables, one of ordinary skill in the art can apply the frequencies to any given polypeptide sequence, and produce a polynucleic acid fragment of a codon-optimized coding region which encodes the polypeptide, but which uses codons optimal for a given species.

Previous codon optimization methods have been disclosed in the art, wherein a polynucleic acid sequence is adjusted based on the codon usage of the host organism. To obtain high expression of heterologous genes in bacteria it may be preferred to reengineer said genes so that they are more efficiently expressed in bacterial cells. A selected coding sequence is traditionally modified by altering the genetic code thereof to match that employed by the bacterial host cell, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis.

As such, the btbooster (BTB) nucleic acid molecule of SEQ ID NO: 3 was optimized for expression in *Escherichia*

*coli*. see International Pat. App. WO2009023639. Codon usage was selected based upon preferred *E. coli*/bacterial codon usage. Accordingly, BTB was redesigned such that the protein is encoded by codons having a bias toward *E. coli*/bacterial usage to increase the efficiency of transcription and translation of the BTB coding sequence and to facilitate DNA manipulation steps. In doing so, expression of BTB in *Pseudomonas fluorescens* results in average levels of protein production.

The novel codon optimization method of the subject disclosure departs from the protocols previously described in the art. The novel codon optimization method disclosed within this application describes the usage of a selected coding sequence which is modified by altering the genetic code thereof to match that employed by a plant, specifically the codon usage of *Zea mays* (maize). The usage of plant codons to encode a polynucleotide sequence which is expressed in bacteria, wherein codon usage from an organism that is classified in a different phylogenetic kingdom, unexpectedly resulted in the robust production of large quantities of recombinant proteins via the *Pseudomonas fluorescens* expression system.

The following definitions are used herein and should be referred to for interpretation of the claims and the specification. Unless otherwise noted, all U.S. patents and U.S. patent applications referenced herein are incorporated by reference in their entirety.

As used herein, the indefinite articles "a" and "an" preceding an element or component of the disclosure are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the terms "comprising" and "including" mean the presence of the stated features, integers, steps, or components as referred to in the claims, but that it does not preclude the presence or addition of one or more other features, integers, steps, components or groups thereof. This means a composition, a mixture, a process, a method, an article, or an apparatus that "comprises" or "includes" a list of elements is not limited to only those elements but may include others not expressly listed or inherent to it. As used herein, "or" refers to an inclusive and an exclusive "or". For example, a condition A or B is satisfied by any one of the following: A is true (or present) and B is false (or not present), A is false (or not present) and B is true (or present), and both A and B are true (or present).

As used herein, the term "about" refers to modifying the quantity of an ingredient or reactant of the disclosure or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "invention" or "present invention" or "subject invention" is a non-limiting term and is intended to encompass all possible variations as described in the specification and recited in the claims.

As used herein, the terms "polypeptide" and "peptide" will be used interchangeably to refer to a polymer of two or more amino acids joined together by a peptide bond. In one aspect, this term also includes post expression modifications of the polypeptide, for example, glycosylations, acetylations, phosphorylations and the like. Included within the definition are, for example, peptides containing one or more analogues of an amino acid or labeled amino acids and peptidomimetics. The peptides may comprise L-amino acids.

As used herein, the terms "peptide of interest", "POI", "gene product", "target gene product", "recombinant protein" "protein" and "target coding region gene product" refer to the desired heterologous peptide/protein product encoded by the recombinantly expressed foreign gene. The peptide of interest may include any peptide/protein product including, but not limited to proteins, fusion proteins, enzymes, peptides, polypeptides, and oligopeptides. The peptide of interest ranges in size from 2 to 398 amino acids in length.

As used herein, the term "construct" refers to a series of contiguous nucleic acids useful for modulating the genotype or phenotype of an organism. Non-limiting examples of genetic constructs include but are not limited to a nucleic acid molecule, an open reading frame, a gene, an expression cassette, a vector, a plasmid and the like.

As used herein, the term "endogenous gene" refers to a native gene in its natural location in the genome of an organism.

As used herein, a "foreign gene" refers to a gene not normally found in the host organism, but that is introduced into the host organism by gene transfer. Foreign genes can comprise native genes inserted into a non-native organism, or chimeric genes.

As used herein, the term "heterologous" with respect to sequence within a particular organism/genome indicates that the sequence originates from a foreign species, or, if from the same species, is substantially modified from its native form in composition and/or genomic locus by deliberate human intervention. Thus, for example, heterologous gene expression refers to the process of expressing a gene from one organism/genome by placing it into the genome of a different organism/genome.

As used herein, the term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The term "genetically engineered" or "genetically altered" means the scientific alteration of the structure of genetic material in a living organism. It involves the production and use of recombinant DNA. It can be used to delineate the genetically engineered or modified organism from the naturally occurring organism. Genetic engineering may be done by a number of techniques known in the art, such as gene replacement, gene amplification, gene disruption, transfection, transformation using plasmids, viruses, or other vectors. A genetically modified organism, e.g. genetically modified microorganism, is also often referred to as a recombinant organism, e.g. recombinant microorganism.

Expression "regulatory sequences" refers collectively to promoter sequences, ribosome binding sites, transcription termination sequences, upstream regulatory domains, enhancers, and the like, which collectively provide for the transcription and translation of a coding sequence in a host cell. Not all of these control sequences need always be present in a recombinant vector so long as the desired gene is capable of being transcribed and translated.

"Recombination" refers to the reassortment of sections of DNA or RNA sequences between two DNA or RNA molecules. "Homologous recombination" occurs between two DNA molecules which hybridize by virtue of homologous or complementary nucleotide sequences present in each DNA molecule.

The terms "stringent conditions" or "hybridization under stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern blot and Northern blot hybridizations are sequence dependent, and are different under varying environmental parameters. An extensive guide to the hybridization of nucleic acids is found in Tijssen (1993) Laboratory Techniques in Biochemistry and Molecular Biology—Hybridization with Nucleic Acid Probes; part I, chapter 2, Overview of principles of hybridization and the strategy of nucleic acid probe assays, Elsevier, New York. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or Northern blot is 50% formamide with 1 mg of heparin at 42° C., with the hybridization being carried out overnight. An example of a highly stringent wash condition is 0.15 M NaCl at 72° C. for about 15 minutes. An example of a stringent wash condition is a 0.2×SSC wash at 65° C. for 15 minutes (see, Sambrook et al. (1989) Molecular Cloning—A Laboratory Manual (2nd ed.) Vol. 1-3, Cold Spring Harbor Laboratory, Cold Spring Harbor Press, NY, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The disclosure also relates to an isolated polynucleotide hybridizable under stringent conditions, preferably under highly stringent conditions, to a polynucleotide as of the present disclosure.

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, most preferably at least 95% identical to each other typically remain hybridized to each other.

In one embodiment, a nucleic acid of the disclosure is at least 40%, 45%, 50%, 55%, 60%, 65%, 70%, 75%, 80%, 85%, 90%, 91%, 92%, 93%, 94%, 95%, 96%, 97%, 98%, 99%, or more identical to a nucleic acid sequence shown in this application or the complement thereof.

Another non-limiting example of stringent hybridization conditions are hybridization in 6× sodium chloride/sodium citrate (SSC) at about 45° C., followed by one or more washes in 1×SSC, 0.1% SDS at 50° C., preferably at 55° C. more preferably at 60° C. and even more preferably at 65° C.

Highly stringent conditions can include incubations at 42° C. for a period of several days, such as 2-4 days, using a labeled DNA probe, such as a digoxigenin (DIG)-labeled DNA probe, followed by one or more washes in 2×SSC, 0.1% SDS at room temperature and one or more washes in 0.5×SSC, 0.1% SDS or 0.1×SSC, 0.1% SDS at 65-68° C. In particular, highly stringent conditions include, for example, 2 hours (h) to 4 days incubation at 42° C. using a DIG-labeled DNA probe (prepared by e.g. using a DIG labeling system; Roche Diagnostics GmbH, 68298 Mannheim, Germany) in a solution such as DigEasyHyb solution (Roche Diagnostics GmbH) with or without 100 μg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

In some embodiments an isolated nucleic acid molecule of the disclosure that hybridizes under highly stringent conditions to a nucleotide sequence of the disclosure can correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein).

A skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those disclosed in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Techniques for determining polynucleic acid and amino acid sequence identity are known in the art. Typically, such techniques include determining the polynucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100.

In addition, methods to determine sequence identity and similarity are codified in publicly available computer programs. Sequence alignments and percent identity calculations can be performed, for example, using the AlignX program of the VECTOR NTI® suite (Invitrogen, Carlsbad, Calif.) or MEGALIGN™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, *CABIOS.* 5:151-153 (1989); Higgins, D. G. et al., *Comput. Appl. Biosci.,* 8:189-191 (1992)) and found in the MEGALIGN™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MEGALIGN™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that are originally load with the software when first initialized.

A preferred embodiment of the present disclosure includes an expression vector which includes the codon optimized polynucleic acid for expression in *Pseudomonas fluorescens*. The expressible coding sequences will be operatively attached to a transcription promoter capable of functioning in the chosen host cell, as well as all other required transcription and translation regulatory elements.

The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The vector will typically comprise one or more phenotypic selectable markers and an origin of replication to ensure maintenance of the vector and to, if desirable, provide amplification within the host. Suitable hosts for transformation in accordance with the present disclosure include various species within the genera *Pseudomonas*, and particularly preferred is the host cell strain of *P. fluorescens*.

In one embodiment, the vector further comprises a coding sequence for expression of a protein or polypeptide of interest, operably linked to the secretion signal disclosed herein. The recombinant proteins and polypeptides can be expressed from polynucleotides in which the target polypeptide coding sequence is operably linked to the leader sequence and transcription and translation regulatory elements to form a functional gene from which the host cell can express the protein or polypeptide. The coding sequence can be a native coding sequence for the target polypeptide, if available, but will more preferably be a coding sequence that has been selected, improved, or optimized for use in the selected expression host cell: for example, by synthesizing the gene to reflect the codon use bias of *Zea mays*. In a preferred embodiment of the disclosure, the host species is a *P. fluorescens*, and the codon bias of *Zea mays* is utilized when designing both the signal sequence and/or the protein or polypeptide sequence. The gene(s) are constructed within or inserted into one or more vector(s), which can then be transformed into the expression host cell.

Other regulatory elements may be included in a vector (also termed "expression construct"). Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" polypeptide coding sequences, which facilitates identification, separation, purification, and/or isolation of an expressed.

A polypeptide encoding gene according to the present disclosure can include, in addition to the protein coding sequence, the following regulatory elements operably linked thereto: a promoter, a ribosome binding site (RBS), a transcription terminator, translational start and stop signals. Useful RBSs can be obtained from any of the species useful as host cells in expression systems according to the present disclosure, preferably from the selected host cell. Many specific and a variety of consensus RBSs are known, e.g., those described in and referenced by D. Frishman et al., Starts of bacterial genes: estimating the reliability of computer predictions, Gene 234(2):257-65 (8 Jul. 1999); and B. E. Suzek et al., A probabilistic method for identifying start codons in bacterial genomes, Bioinformatics 17(12): 1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a *Rhodococcus* species and its expression in *Escherichia coli*, Eur. J. Biochem. 181(3):563-70 (1989)(native RBS sequence of AAGGAAG). Further examples of methods, vectors, and translation and transcription elements, and other elements useful in the present disclosure are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to protein Wilcox.

Transcription of the DNA encoding the proteins of the present disclosure can be increased by inserting an enhancer sequence into the vector or plasmid. Typical enhancers are cis-acting elements of DNA, usually about from 10 to 300 bp in size that act on the promoter to increase its transcription. Examples include various enhancers known in the art.

Generally, the recombinant expression vectors will include origins of replication and selectable markers permitting transformation of the host cell and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. The heterologous structural sequence is assembled in appropriate phase with translation initiation and termination sequences, and preferably, the secretion sequence capable of directing secretion of the translated polypeptide. Optionally, the heterologous sequence can encode a fusion polypeptide including an N-terminal identification polypeptide imparting desired characteristics, e.g., stabilization or simplified purification of expressed recombinant product.

Vectors are known in the art for expressing recombinant proteins in host cells, and any of these may be used for expressing the genes according to the present disclosure. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Further examples can include pALTER-Ex1, pALTER-Ex2, pBAD/His, pBAD/Myc-His, pBAD/gIII, pCal-n, pCal-n-EK, pCal-c, pCal-Kc, pcDNA 2.1, pDUAL, pET-3a-c, pET 9a-d, pET-11a-d, pET-12a-c, pET-14b, pET15b, pET-16b, pET-17b, pET-19b, pET-20b(+), pET-21a-d(+), pET-22b(+), pET-23a-d(+), pET24a-d(+), pET-25b(+), pET-26b(+), pET-27b(+), pET28a-c(+), pET-29a-c(+), pET-30a-c(+), pET31b(+), pET-32a-c(+), pET-33b(+), pET-34b(+), pET35b(+), pET-36b(+), pET-37b (+), pET-38b(+), pET-39b(+), pET-40b(+), pET411a-c(+), pET-42a-c(+pET43a-c(+), pETBlue-1, pETBlue-2, pET-Blue-3, pGEMEX-1, pGEMEX-2, pGEX1λT, pGEX-2T, pGEX-2TK3X, pGEX4T, pGEX-5X, pGEX-6P, pHAT10/11/12, pHAT20, pHAT-GFPuv, pKK223-3, pLEX, pMAL-c2X, pMAL-c2E, pMAL-c2g, pMAL-p2X, pMAL-p2E, pMAL-p2G, pProEX HT, pPROLar.A, pPROTet.E, pQE-9, pQE-16, pQE-30/31/32, pQE40, pQE-50, pQE-70, pQE-80/81/82L, pQE-100, pRSET, and pSE280, pSE380, pSE420, pThioHis, pTrc99A, pTrcHis, pTrcHis2, pTriEx-1, pTriEx-2, pTrxFus. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1):11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1): 145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1):477-80 (January 1990); D. O. Wood et al., in J. Bact. 145(3):1448-51 (March 1981); and R. Holtwick et al., in Microbiology 147(Pt 2):337-44 (February 2001).

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF110 and derivatives thereof are particularly useful vectors in the present disclosure. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF110-based plasmid, pTJS260 (see U.S. Pat. No. 5,169,760 to Wilcox), which carries a regulated tetracycline resistance marker and the replication and mobilization loci from the RSF 1010 plasmid. Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC4803 or a derivative thereof, is used as the expression vector. In a preferred embodiment the pDOW1169 or pDAB1817 expression plasmid is used as the expression vector.

The plasmid can be maintained in the host cell by inclusion of a selection marker gene in the plasmid. This may be an antibiotic resistance gene(s), where the corresponding antibiotic(s) is added to the fermentation medium, or any other type of selection marker gene known in the art, e.g., a prototrophy-restoring gene where the plasmid is used in a host cell that is auxotrophic for the corresponding trait, e.g., a biocatalytic trait such as an amino acid biosynthesis or a nucleotide biosynthesis trait, or a carbon source utilization trait.

The promoters used in accordance with the present disclosure may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism. see, J. Sanchez-Romero & V. De Lorenzo (1999) Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (ASM Press, Washington, D.C.); H. Schweizer (2001) Vectors to express foreign genes and techniques to monitor gene expression for Pseudomonads, Current Opinion in Biotechnology, 12:439-445; and R. Slater & R. Williams (2000) The Expression of Foreign DNA in Bacteria, in Molecular Biology and Biotechnology (J. Walker & R. Rapley, eds.) pp. 125-54 (The Royal Society of Chemistry, Cambridge, UK)).

A promoter having the polynucleotide sequence of a promoter native to the selected bacterial host cell may also be used to control expression of the transgene encoding the target polypeptide, e.g, a *Pseudomonas anthranilate* or benzoate operon promoter (described as; Pant or Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present disclosure. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

By way of example, where a lac family promoter is utilized, a lacI gene can also be present in the system. The lacI gene, which is (normally) a constitutively expressed gene, encodes the Lac repressor protein (LacD protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl β-D-1-thiogalactopyranoside, also called "isopropylthiogalactoside").

For expression of a protein or polypeptide of interest, any plant promoter may also be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: *Genetic Engineering of Plants*, Kosuge et al., eds., pp. 211-227). In addition, virtually all promoters include additional upstream activating sequences or enhancers (Benoist and Chambon (1981) Nature 290:304-310; Gruss et al. (1981) Proc. Nat. Acad. Sci. 78:943-947; and Khoury and Gruss (1983) Cell 27:313-314) extending from around ~100 bp to ~1,000 bp or more upstream of the transcription initiation site.

Transformation of the host cells with the vector(s) disclosed herein may be performed using any transformation methodology known in the art, and the bacterial host cells may be transformed as intact cells or as protoplasts (i.e. including cytoplasts). Exemplary transformation methodologies include 'poration methodologies, e.g., electroporation, protoplast fusion, bacterial conjugation, and divalent cation treatment (calcium chloride $CaCl_2$ treatment or $CaCl_2/Mg^{2+}$ treatment), or other well known methods in the art. See, e.g., Morrison, *J. Bact.*, 132:349-351 (1977); Clark-Curtiss & Curtiss, *Methods in Enzymology*, 101:347-362 (Wu et al., eds, 1983), Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

In an embodiment, the host cell can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluore-*

*scens* Pf-5 (ATCC BAA-477); *Pseudomonas fluorescens* SBW25; and *Pseudomonas fluorescens* subsp. *cellulosa* (NCIMB 10462).

Additional, *P. fluorescens* strains that can be used in the present disclosure include *Pseudomonas fluorescens* Migula and *Pseudomonas fluorescens* Loitokitok, having the following ATCC designations: NCIB 8286; NRRL B-1244; NCIB 8865 strain CO1; NCIB 8866 strain $CO_2$; 1291 [ATCC 17458]; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323]; NIH 11; den Dooren de Jong 216; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212 [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21 [IFO 3081]; N; PYR; PW; D946-B83 [BU 2183; FERM-P 3328]; P-2563 [FERM-P 2894; IFO 13658]; IAM-1 126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In one embodiment, the host cell can be any cell capable of producing a protein or polypeptide of interest, including a *P. fluorescens* cell as described above. The most commonly used systems to produce proteins or polypeptides of interest include certain bacterial cells, particularly *E. coli*, because of their relatively inexpensive growth requirements and potential capacity to produce protein in large batch cultures. Yeast is also used to express biologically relevant proteins and polypeptides, particularly for research purposes. Systems include *Saccharomyces cerevisiae* or *Pichia pastoris*. These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced using the insect cell expression system. Mammalian cell expression systems, such as Chinese Hamster Ovary cells (CHO cells), have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to; a tobacco cell, corn cell, a cell from an *Arabidopsis* species, potato cell, or rice cell. In another embodiment, a multicellular organism is analyzed or is modified in the process, including but not limited to a transgenic organism. Techniques for analyzing and/or modifying a multicellular organism are generally based on techniques described for modifying cells described below.

In another embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans", a chapter of the On-Line Biology Book, provided by Dr M J Farabee of the Estrella Mountain Community College, Arizona, USA at the website www.em-c.maricotpa.edu/faculty/farabee/BIOBK/BioBookDiversity. In certain embodiments, the host cell can be a *Pseudomonas* cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey cell, a primate cell, or a human cell.

In one embodiment, the host cell can be a member of any of the bacterial taxa. The cell can, for example, be a member of any species of eubacteria. The host can be a member of any one of the following taxa; Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Thermus (Thermales), or Verrucomicrobia. In a embodiment of a eubacterial host cell, the cell can be a member of any species of eubacteria, excluding Cyanobacteria.

The bacterial host can also be a member of any species of Proteobacteria. A proteobacterial host cell can be a member of any one of the following taxa; Alphaproteobacteria, Betaproteobacteria, Gammaproteobacteria, Deltaproteobacteria, or Epsilonproteobacteria.

In one embodiment of a Gammaproteobacterial host, the host will be member of any one of the following taxa; Aeromonadales, Alteromonadales, Enterobacteriales, Pseudomonadales, or Xanthomonadales; or a member of any species of the Enterobacteriales or Pseudomonadales. In one embodiment, the host cell can be of the order of Enterobacteriales, the host cell will be a member of the family Enterobacteriaceae, or may be a member of any one of the genera *Erwinia, Escherichia*, or *Serratia*; or a member of the genus *Escherichia*. Where the host cell is of the order Pseudomonadales, the host cell may be a member of the family Pseudomonadaceae, including the genus *Pseudomonas*. Gamma Proteobacteria hosts include members of the species *Escherichia coli* and members of the species *Pseudomonas fluorescens*.

Other *Pseudomonas* organisms may also be useful. *Pseudomonas* and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974)(The Williams & Wilkins Co., Baltimore, Md., USA)(hereinafter "Bergey (1974)").

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus

*Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciens* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym "Methylococcaceae").

Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera*.

In one aspect of the present disclosure, processes of expressing recombinant polypeptides for use in improved protein production are provided.

In one embodiment of the present disclosure, at least one recombinant polypeptide can be expressed in a *Pseudomonas* cell, wherein the recombinant protein is expressed from a *Zea mays* codon optimized polynucleotide sequence. Alternatively, more than one recombinant polypeptide can be expressed in a *Pseudomonas* cell, wherein the polynucleic acids encoding the recombinant polypeptides are encoded by a *Zea mays* codon optimized polynucleotide sequence contained on the same vector, or alternatively, on multiple vectors.

In another aspect, the present disclosure provides a method of producing a recombinant polypeptide comprising transforming a bacterial host cell that is a member of the *Pseudomonas* genus and closely related bacteria having at least one chromosomally inserted copy of a Lac repressor protein encoding a lad transgene, or derivative thereof such as lacI$^{Q1}$, which transgene is other than part of a whole or truncated structural gene containing PlacI-lacI-lacZYA construct with a nucleic acid construct encoding at least one target recombinant polypeptide. The nucleic acid encoding at least one target recombinant polypeptide can be operably linked to a Plac family promoter, in which all of the Plac family promoters present in the host cell are regulated by Lac repressor proteins expressed solely from the lad transgene inserted in the chromosome. Optionally, the expression system is capable of expressing the target polypeptide at a total productivity of at least 0.02 g/L to at least 10 g/L. Preferably, the expression system is capable of expressing the target polypeptide at a total productivity of polypeptide of at least 0.02 g/L, 0.1 g/L, 0.5 g/L, 1 g/L, 2.5 g/L, 5 g/L, or at least 10 g/L.

The present disclosure further provides an improved codon optimization method which results in the production of high levels or greater quantities of recombinant protein via fermentation. In a preferred embodiment, the *Pseudomonas fluorescens* expression system includes a host cell and a vector described above comprising a polynucleotide sequence encoding a protein or polypeptide that is codon optimized to contain *Zea mays* preferred codons. The system can also include a fermentation medium. In one embodiment, the system includes a *Pseudomonas* expression medium.

As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, a mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly preferred. All such media can be utilized for the expression of proteins and are considered as preferred embodiments of a *Pseudomonas* expression medium.

Prior to transformation of the host cell with a nucleic acid construct encoding a prototrophic enabling enzyme, the host cell can be maintained in a media comprising a supplemental metabolite, or analogue thereof that complements the auxotrophy. Following transformation, the host cell can be grown in a media that is lacking the complementary metabolite that the host cell is auxotrophic for. In this way, host cells that do not contain the selection marker enabling prototrophy are selected against. Likewise cells expressing recombinant proteins from expression vectors containing an antibiotic resistance selection marker gene can be maintained prior to transformation on a medium lacking the associated antibiotic used for selection. After transformation and during the fermentation, an antibiotic can be added to the medium, at concentrations known in the art, to select against non-transformed and revertant cells.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli, in J. Bact. 60:17-28 (1950)). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A particular mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at minimal levels.

The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115™. Then, after heat sterilization (such as at approximately 121° C.), sterile solutions of glucose $MgSO_4$ and thiamine-HCL can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for high cell density cultivation (HCDC) for growth of Pseudomonas species and related bacteria. The HCDC can start as a batch process which is followed by two-phase fed-batch cultivation. After unlimited growth in the batch phase, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of Escherichia coli at controlled specific growth rate" J Biotechnol: 20(1) 17-27.

The expression system according to the present disclosure can be cultured in any fermentation format. For example, batch, fed-batch, semi-continuous, and continuous fermentation modes may be employed herein.

The expression systems according to the present disclosure are useful for transgene expression at any scale (i.e. volume) of fermentation. Thus, e.g., microliter-scale, centiliter scale, and deciliter scale fermentation volumes may be used. In addition, larger scale fermentations including fermentations greater than 1 Liter scale can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 50 Liters, 1,000 Liters, 2,000 Liters, 5,000 Liters, 10,000 Liters, 50,000 Liters or 100,000 Liters.

In the present disclosure, growth, culturing, and/or fermentation of the transformed host cells is performed within a temperature range permitting survival of the host cells, preferably a temperature within the range of about 4° C. to about 55° C., inclusive.

An additional advantage in using Pseudomonas fluorescens in expressing recombinant proteins includes the ability of Pseudomonas fluorescens to be grown in high cell densities compared to E. coli or other bacterial expression systems. To this end, Pseudomonas fluorescens expressions systems according to the present disclosure can provide a cell density of about 20 g/L or more. The Pseudomonas fluorescens expressions systems according to the present disclosure can likewise provide a cell density of at least about 70 g/L, as stated in terms of biomass per volume, the biomass being measured as dry cell weight.

In one embodiment, the cell density will be at least 20 g/L. In another embodiment, the cell density will be at least 25 g/L, 30 g/L, 35 g/L, 40 g/L, 45 g/L, 50 g/L, 60 g/L, 70 g/L 80 g/L, 90 g/L, 100 g/L, 110 g/L, 120 g/L, 130 g/L, 140 g/L, or at least 150 g/L.

In another embodiment, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

The recombinant proteins produced according to this disclosure may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); A K Patra et al., Protein Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example., Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QIAGEN, Inc., Chatsworth, Calif.

Detection of the expressed protein is achieved by methods known in the art and includes, for example, SDS-PAGE (PolyAcrylamide Gel Electrophoresis), radioimmunoas says, Western blotting techniques, or immunoprecipitation.

The recombinantly produced and expressed protein can be recovered and purified from the recombinant cell cultures by numerous methods, for example, high performance liquid chromatography (HPLC) can be employed for final purification steps, as necessary.

Certain proteins expressed in this disclosure may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF (phenylmethanesulfonylfluoride). The cell suspension is typically lysed using 2-3 passages through a French Press. The cell suspension can also be homogenized using a Polytron™ (Brinkman Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 6 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

Alternatively, it is possible to purify the recombinant proteins or peptides from the host periplasm. After lysis of the host cell, when the recombinant protein is exported into the periplasm of the host cell, the periplasmic fraction of the bacteria can be isolated by cold osmotic shock in addition to other methods known to those skilled in the art. To isolate recombinant proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM $MgSO_4$ and kept in an ice bath for approximately 10 minutes. The cell suspension can be centrifuged and the supernatant decanted and saved. The recombinant proteins present in the supernatant can be separated from the host proteins by standard separation techniques well known to those of skill in the art.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater or lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate.

Recombinant proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM sodium acetate pH 6 buffer plus 200 mM NaCl. Alternatively, the protein can be refolded while immobilized on a column, such as the Ni NTA column by using a linear 6M-7M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM immidazole Immidazole can be removed by a final dialyzing step or diafiltration against PBS or 50 mM Tris pH 8.5 buffer plus 200 mM NaCl. The purified protein can be stored at 4° C. or frozen at −80° C.

Other methods include, for example, those that may be described in M H Lee et al., Protein Expr. Purif., 25(1): p. 166-73 (2002), W. K. Cho et al., J. Biotechnology, 77(2-3): p. 169-78 (2000), Ausubel, et al. (1987 and periodic supplements), Deutscher (1990) "Guide to Protein Purification," Methods in Enzymology vol. 182, and other volumes in this series, Coligan, et al. (1996 and periodic Supplements) Current Protocols in Protein Science Wiley/Greene, NY, S. Roe, Protein Purification Techniques: A Practical Approach (Practical Approach Series), Oxford Press (2001); D. Bollag, et al., Protein Methods, Wiley-Lisa, Inc. (1996).

The present disclosure provides improved protein production in bacterial expression systems. Examples of recombinant polypeptides that can be used in the present disclosure include polypeptides derived from prokaryotic and eukaryotic organisms. Such organisms include organisms from the domain Archea, Bacteria, Eukarya, including organisms from the following Kingdoms; Protista, Fungi, Plantae, and Animalia.

Types of proteins that can be utilized in the present disclosure include non-limiting examples such as enzymes, which are responsible for catalyzing the thousands of chemical reactions of the living cell including; keratin, elastin, and collagen, which are important types of structural, or support, proteins; hemoglobin and other gas transport proteins; ovalbumin, casein, and other nutrient molecules; antibodies, which are molecules of the immune system; protein hormones, which regulate metabolism; and proteins that perform mechanical work, such as actin and myosin, and including other contractile muscle proteins.

All patents, patent applications, provisional applications, and publications referred to or cited herein are incorporated by reference in their entirety to the extent they are not inconsistent with the explicit teachings of this specification The following examples are included to illustrate procedures for practicing the disclosure and to demonstrate certain preferred embodiments of the disclosure. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the disclosure. Unless otherwise indicated, all percentages are by weight and all solvent mixture proportions are by volume unless otherwise noted.

The following abbreviations are used unless otherwise indicated.
  bp base pair
  ° C. degrees Celsius
  DNA deoxyribonucleic acid
  EDTA ethylenediaminetetraacetic acid
  kb kilobase
  μg microgram
  μL microliter
  mL milliliter
  M molar mass
  PCR polymerase chain reaction
  PTU plant transcription unit
  SDS sodium dodecyl sulfate
  SSC a buffer solution containing a mixture of sodium chloride and sodium citrate, pH 7.0
  TBE a buffer solution containing a mixture of Tris base, boric acid and EDTA, pH 8.3

EXAMPLES

Example 1

Maize Codon Optimization of BTB Polynucleotide Sequence

Analysis of the BTB nucleic acid coding sequence revealed the presence of several sequence motifs that were believed to be detrimental to optimal expression, as well as a non-optimal codon composition for expression of the protein. Thus, an achievement of the present disclosure is design of a maize optimized gene encoding BTB to generate a DNA sequence that can be optimally expressed in *Pseudomonas fluorescens*, and in which the sequence modifications do not hinder translation or create mRNA instability.

Due to the plasticity afforded by the redundancy/degeneracy of the genetic code (i.e., some amino acids are specified by more than one codon), evolution of the genomes in different organisms or classes of organisms has resulted in differential usage of synonymous codons. This "codon bias" is reflected in the mean base composition of protein coding regions. For example, organisms having genomes with relatively low G+C contents utilize more codons having A or T in the third position of synonymous codons, whereas those having higher G+C contents utilize more codons having G or C in the third position. Further, it is thought that the presence of "minor" codons within an mRNA may reduce the absolute translation rate of that mRNA, especially when the relative abundance of the charged tRNA corresponding to the minor codon is low. An extension of this reasoning is that the diminution of translation rate by individual minor codons would be at least additive for multiple minor codons. Therefore, mRNAs having high relative contents of minor codons would have correspondingly low translation rates. This rate could be reflected by correspondingly low levels of the encoded protein.

In engineering a gene encoding BTB for robust expression within *Pseudomonas fluorescens*, the incorporation of codons from maize unexpectedly resulted in the production of high levels of BTB expressed protein. Multiple publicly available DNA sequence databases exist wherein one may find information about the codon distribution of plant and microbial genomes or the protein coding regions of various plant and microbial genes. The codon bias is the statistical distribution of codons that an organism uses for coding the amino acids of its proteins. The preferred codon usages for dicots or monocots (maize) are shown in Table 1.

TABLE 1

| A Amino Acid | B Codon | C Weighted Average | D Maize % | E Dicot % | F Amino Acid | G Codon | H Weighted Average | I Maize % | J Dicot % |
|---|---|---|---|---|---|---|---|---|---|
| ALA (A) | GCA | 25.5 | 18 | 25 | LEU (L) | CTA | DNU | 8 | 8 |
| 100 | GCC | 35.6 | 34 | 27 | 100 | CTC | 34.3 | 26 | 19 |
| | GCG | DNU | 24 | 6 | | CTG | DNU | 29 | 9 |
| | GCT | 39.0 | 24 | 42 | | CTT | 34.3 | 17 | 28 |
| ARG (R) | AGA | 27.4 | 15 | 30 | | TTA | DNU | 5 | 10 |
| 100 | AGG | 31.5 | 26 | 25 | | TTG | 31.4 | 15 | 26 |
| | CGA | DNU | 9 | 8 | LYS (K) | AAA | 30.6 | 22 | 39 |
| | CGC | 21.7 | 24 | 11 | 100 | AAG | 69.4 | 78 | 61 |
| | CGG | DNU | 15 | 4 | MET (M) | ATG | 100 | 100 | 100 |
| | CGT | 19.4 | 11 | 21 | PHE (F) | TTC | 63.2 | 71 | 55 |
| ASN (N) | AAC | 61.4 | 68 | 55 | 100 | TTT | 36.8 | 29 | 45 |
| 100 | AAT | 38.6 | 32 | 45 | PRO (P) | CCA | 41.4 | 26 | 42 |
| ASP (D) | GAC | 52.6 | 63 | 42 | 100 | CCC | 25.3 | 24 | 17 |
| 100 | GAT | 47.4 | 37 | 58 | | CCG | DNU | 28 | 9 |
| CYS (C) | TGC | 61.8 | 68 | 56 | | CCT | 33.3 | 22 | 32 |
| 100 | TGT | 38.2 | 32 | 44 | SER (S) | AGC | 26.0 | 23 | 18 |
| END | TAA | | 20 | 48 | 100 | AGT | DNU | 9 | 14 |
| 100 | TAG | | 21 | 19 | | TCA | 22.4 | 16 | 19 |
| | TGA | | 59 | 33 | | TCC | 26.3 | 23 | 18 |
| GLN (Q) | CAA | 48.4 | 38 | 59 | | TCG | DNU | 14 | 6 |
| 100 | CAG | 51.6 | 62 | 41 | | TCT | 25.4 | 15 | 25 |
| GLU (E) | GAA | 38.8 | 29 | 49 | THR (T) | ACA | 28.0 | 21 | 27 |
| 100 | GAG | 61.2 | 71 | 51 | 100 | ACC | 39.5 | 37 | 30 |
| GLY (G) | GGA | 28.5 | 19 | 38 | | ACG | DNU | 22 | 8 |
| 101 | GGC | 29.0 | 42 | 16 | | ACT | 32.5 | 20 | 35 |
| | GGG | 16.0 | 20 | 12 | TRP (W) | TGG | 100 | 100 | 100 |
| | GGT | 26.6 | 20 | 33 | TYR (Y) | TAC | 65.0 | 73 | 57 |

TABLE 1-continued

| A<br>Amino<br>Acid | B<br>Codon | C<br>Weighted<br>Average | D<br>Maize<br>% | E<br>Dicot<br>% | F<br>Amino<br>Acid | G<br>Codon | H<br>Weighted<br>Average | I<br>Maize<br>% | J<br>Dicot<br>% |
|---|---|---|---|---|---|---|---|---|---|
| HIS (H) | CAC | 54.1 | 62 | 46 | 100 | TAT | 35.0 | 27 | 43 |
| 100 | CAT | 45.9 | 38 | 54 | VAL (V) | GTA | DNU | 8 | 12 |
| ILE (I) | ATA | 15.9 | 14 | 18 | 100 | GTC | 28.7 | 32 | 20 |
| 100 | ATC | 47.9 | 58 | 37 |  | GTG | 38.0 | 39 | 29 |
|  | ATT | 36.4 | 28 | 45 |  | GTT | 33.3 | 21 | 39 |

Synonymous codon representation from coding regions of monocotyledonous (maize %) and dicotyledonous (dicot %) plant genes are shown in Columns D, E, I, and J.
Values for a balanced-biased codon representation set for a plant-optimized synthetic gene design are in Columns C and H.
DNU is an abbreviation for Do Not Use.

The codon bias can be calculated as the frequency at which a single codon is used relative to the codons for all amino acids. Alternatively, the codon bias may be calculated as the frequency at which a single codon is used to encode a particular amino acid, relative to all the other codons for that amino acid (synonymous codons). In designing coding regions for plant or bacterial expression of, the primary ("first choice") codons preferred by the plant or bacteria should be determined, as well as the second, third, fourth etc. choices of preferred codons when multiple choices exist. A new DNA sequence can then be designed which encodes the amino acid sequence of the same BTB peptide, but the new DNA sequence differs from the original DNA sequence by the substitution of maize (first preferred, second preferred, third preferred, or fourth preferred, etc.) codons to specify the amino acid at each position within the amino acid sequence. The new sequence is then analyzed for restriction enzyme sites that might have been created by the modifications. The identified sites are further modified by replacing the codons with first, second, third, or fourth choice preferred codons. Other sites in the sequence which could affect transcription or translation of the gene of interest are the stem loop structures, exon:intron junctions (5' or 3'), poly A addition signals, or RNA polymerase termination signals; these sites are removed by the substitution of plant codons. The sequence is further analyzed and modified to reduce the frequency of TA or CG doublets. In addition to the doublets, G or C sequence blocks that have more than about six residues that are the same can affect transcription or translation of the sequence. Therefore, these blocks are advantageously modified by replacing the codons of first or second choice, etc. with the next preferred codon of choice.

One may thus use a variety of methods to produce a gene as described herein. An example of one such approach is further illustrated in PCT App. WO 97/13402. Thus, synthetic genes that are functionally equivalent to the BTB gene of the subject disclosure can be used to transform hosts, including *Pseudomonas fluorescens*. Additional guidance regarding the production of synthetic genes can be found in, for example, U.S. Pat. No. 5,380,831.

To engineer a maize-optimized gene encoding BTB, a DNA sequence was designed to encode the amino acid sequences utilizing a redundant genetic code established from a codon bias table compiled from the protein coding sequences for the particular host plants. In Table 1, Columns D and I present the distributions (in % of usage for all codons for that amino acid) of synonymous codons for each amino acid, as found in the coding regions of monocotyledonous (maize) plants. Columns E and J present the distributions (in % of usage for all codons for that amino acid) of synonymous codons for each amino acid, as found in the coding regions of dicotyledonous plants. Some synonymous codons for some amino acids are found only rarely in plant genes. Usually, a codon was considered to be rarely used if it is represented at about 10% or less of the time to encode the relevant amino acid in genes of either plant type (indicated by DNU in Columns C and H of Table 1). To balance the distribution of the remaining codon choices for an amino acid, a Weighted Average representation for each codon was calculated, using the formula:

Weighted Average % of $C1 = 1/(\% \ C1 + \% \ C2 + \% \ C3 + \text{etc.}) \times \% \ C1 \times 100$ where C1 is the codon in question and % C2, % C3, etc. represent the averages of the % values for the plant optimized sequence of remaining synonymous codons (average % values for the relevant codons are taken from Columns C and H) of Table 1. The Weighted Average % value for each codon is given in Columns C and H of Table 1.

A new DNA sequence which encodes the amino acid sequence of the BTB protein was designed for optimal expression, using a maize codon distribution of frequently used codons found in maize plant genes. The new DNA sequence differs from the original DNA sequences encoding BTB by the substitution of maize (first preferred, second preferred, third preferred, or fourth preferred) codons to specify the appropriate amino acid at each position within the protein amino acid sequence. Design of the maize-optimized DNA sequences were initiated by reverse-translation of the protein sequences of the BTB protein sequence (SEQ ID NO:1; International Pat. App. WO2009023639). The BTB sequence was reverse-translated using a maize codon bias table constructed from Table 1; Columns E and J. The initial sequence was then modified by compensating codon changes (while retaining overall weighted average codon representation) to remove or add restriction enzyme recognition sites, remove highly stable intrastrand secondary structures, and remove other sequences that might be detrimental to cloning manipulations or expression of the engineered gene in plants. The DNA sequence was then re-analyzed for restriction enzyme recognition sites that might have been created by the modifications. The identified sites were further modified by replacing the relevant codons with first, second, third, or fourth choice preferred codons. Other sites in the sequences that could affect transcription or translation of the gene of interest include the exon:intron junctions (5' or 3'), poly A addition signals, or RNA polymerase termination signals. The modified sequences were further analyzed and further modified to reduce the frequency of TA or CG doublets, and to increase the frequency of TG or CT doublets. In addition to these doublets, sequence blocks that have more than about six consecutive residues of [G+C] or [A+T] can affect transcription or translation of the sequence. Therefore, these sequence blocks were also modified by replacing the codons of first or second choice, etc. with other preferred codons of choice. Rarely used maize-codons are not included to a substantial extent in the gene design, being used only when necessary to accommodate a different design criterion than codon composition per se (e.g. addition or deletion of restriction enzyme recognition sites).

The newly designed, maize optimized BTB polynucleotide sequence is listed in SEQ ID NO:2. The resulting DNA sequence has a higher degree of maize codon diversity, a desirable base composition, contains strategically placed restriction enzyme recognition sites, and lacks sequences that might interfere with transcription of the gene, or translation of the product mRNA.

Once a maize-optimized DNA sequence has been designed on paper or in silico, actual DNA molecules can be synthesized in the laboratory to correspond in sequence precisely to the designed sequence. Such synthetic DNA molecules can be cloned and otherwise manipulated exactly as if they were derived from natural or native sources. Synthesis of DNA fragments comprising SEQ ID NO:2 containing additional sequences such as additional stop codons, 5' and 3' restriction sites for cloning, and the addition of a Shine-Delgarno sequence were performed by commercial suppliers. The synthetic DNA was then cloned into expression vectors and transformed into *Pseudomonas fluorescens* as described in the Examples below.

Example 2

Preparation of *E. coli* Codon Optimized BTB Fragment

The *E. coli* codon optimized coding sequence of BTB (SEQ ID NO:3) was PCR amplified using PHUSION® High-Fidelity DNA Polymerase (Finnzymes, Lafayette, (20). The total reaction was 40 μL and contained 2 μL template DNA (100 ng/μL), 1 μL forward primer: SEQ ID NO:4 (10 pMol/μL), 1 μL reverse primer: SEQ ID NO:5 (10 pMol/μL), 8 μL HF Buffer, 1 μL dNTP, 1 μL Phusion polymerase, and 26 μL sterile water. PCR condition were 98° C. for five minutes; then 25 cycles of 98° C. denaturing for five seconds, 67° C. annealing for one minute, and 72° C. elongation for one minute; then 1 cycle of 72° C. for five minutes; followed by a 4° C. hold. The PCR product was ~1 kb in length. This PCR product was run on a 1% agarose gel and gel extracted using the QIAquick Gel Extraction Kit™ (Qiagen, Valencia, Calif.) according to the manufacturer's instruction except steps 5 and 9 were omitted. The purified PCR product was then ligated into pCR-BluntII-TOPO vector Kit™ (Invitrogen, Carlsbad, Calif.). The ligation mixture contained 4 μL PCR product, 1 μL salt solution and 1 μL pCR-BluntII-TOPO Vector™. The ligation mixture was left at room temperature for 15 minutes then transformed into Invitrogen Top Ten Cells™. Four microliters (4 μL) of ligation mixture was added to Top Ten™ chemically competent cells. The reaction was incubated on ice for 15 minutes, then heat shocked for 30 seconds at 42° C. The cells were then placed on ice for one minute, then 250 μL SOC was added and the cells recovered at 37° C. for one hour with shaking at 200 rpm. Cells were plated on LB+Kanamycin (Kan, 50 μg/ml)+X-gal overnight at 37° C.

Five colonies were picked and used to inoculate 4 mL LB+Kan (50 μg/ml) overnight cultures which were shaken at 200 rpm at 37° C. Each of the five overnight cultures were mini-prepped using the Macherey-Nagel, NucleoSpin Miniprep Kit™ (Macherey-Nagel, Neumann-Neander-Strasse, Duren, Germany) according to the manufacturer's instructions. Forty microliters (40 μL) of purified plasmid was digested with NheI/SalI in a 50 μL mixture containing 1 μL BSA (New England Biolabs), 5 μL Buffer 4 (NEB), 2 μL NheI (NEB), and 2 μL SalI (NEB). The cocktail was left at 37° C. for one hour then run on a 1% agarose gel and the smaller fragment, approximately 1 kb, was gel extracted with the Qiagen QIAquick Gel Extraction Kit™ (per manufacturer's instruction minus steps 5 and 9).

Example 3

Preparation of Maize Codon Optimized BTB Fragment

A maize codon optimized BTB coding sequence was synthesized by DNA 2.0 (Menlo Park, Calif.). A stab of the glycerol stock was streaked onto an LB+Kan (50 μg/ml) plate and grown overnight at 37° C. The following day, a single colony was picked and grown overnight in 4 mL LB+Kan (50 μg/ml) at 37° C. with shaking at 250 rpm. The plasmid was mini-prepped using NucleoSpin Miniprep Kit™ according to the manufacturer's instructions. The purified plasmid was stored at −20° C. Forty microliters (40 μL) of purified plasmid was digested with NheI/SalI in a 50 μL mixture containing 1 μL BSA (New England Biolabs [NEB], Ipswich, Mass.), 5 μL Buffer 4, 2 μL NheI, and 2 μL SalI. The insert was purified using the Qiagen Plasmid Purification Kit™ protocol with 30 μL EB used to elute the DNA.

Example 4

Preparation of pDOW1169 and pDAB1817 Vectors

Approximately 1 μg of pDOW1169 (U.S. Pat. No. 7,618, 799) plasmid DNA was digested with SpeI/SalI in a 30 μL mixture containing 1 μL BSA, 3 μL Buffer 4, 1 μL SpeI, and 1 μL SalI. The mixture was incubated at 37° C. for one hour then 3 μL of Antarctic Phosphatase (NEB) buffer and 1 μL of Antarctic Phosphatase were added to the mixture. The digestion was incubated at 37° C. for 15 minutes then brought to 70° C. for five minutes to inactivate the phosphatase. Plasmid pDAB1817 (PCT App. WO 2011/075587) was digested with SpeI/XhoI in a 30 μL mixture containing 1 μL BSA, 3 μL Buffer 4, 1 μL SpeI, and 1 μL XhoI and incubated at 37° C. for one hour. The digested plasmids were stored at −20° C. until needed.

Example 5

Ligation of BTB Fragments into pDOW1169 and pDAB1817 Vectors

A 20 μL ligation mixture was made from 8 μL of either the *E. coli* and maize codon optimized BTB fragments digested with NheI/SalI, 2 μL pDOW1169 digested with SpeI/SalI and phosphatase, or 2 μL pDAB1817 digested with SpeI/XhoI, 7 μL sterile water, 2 μL T4 DNA Ligase Buffer (NEB), and 1 μL T4 DNA Ligase (NEB). This ligation mixture was incubated at room temperature overnight then transformed into competent *Pseudomonas* cells the following day.

Example 6

Preparing Pf10 and MB214 Competent Cells

Competent *Pseudomonas fluorescens* cells for the expression of heterologous genes contained on the pDOW1169 and pDAB1817 vectors were prepared. *Pseudomonas fluorescens* strain Pf5 (ATCC BAA-477), which is used for the heterologous expression of genes contained on the pDOW1169 vector, was grown overnight on agar plates containing M9 Minimal media supplemented with the amino acid Uracil. *Pseudomonas fluorescens* strain MB214 (U.S. Pat. No. 7,618,799), the host expression strain for heterologous expression of genes contained on the pDAB1817 vector was grown overnight on LB plates. The following day the plates were scraped off and the cells were re-suspended in 1 mL of 300 mM sterile sucrose. This mixture was spun in a Microfuge™ tube at 14,000 rpm for 2 minutes. The supernatant was discarded while the pellet was re-suspended in 1 mL of 300 mM sterile sucrose. This process was repeated two additional times, and then the final pellet was re-suspended in 1 mL of 300 mM sterile sucrose. The competent cells were left on ice until needed but never stored for more than 8 hours.

Example 7

Electroporation

One-hundred microliters (100 µL) of competent cells were added to a 0.2 cm electroporation cuvette (Bio-Rad, Hercules, Calif.), to this 10 µL of the ligation mixture was added. The cuvette was incubated on ice for five minutes, then electroporated with the following electroporation settings: 2.25 kV/cm, 25 uF and 200Ω. After electroporation, 500 µL S.O.C. was added then transferred to a 14 mL tube. The tube was shaken at 250 rpm and 28° C. for two hours to allow the cells to recover. One-hundred and fifty microliters (150 µL) of each sample was plated on M9 Minimal agar plates with no antibiotics for Pf10 strains transformed with the pDOW1169 vector, or LB+Tet (30 µg/ml) for MB214 strains transformed with the pDAB1817 vector and incubated at 28° C. for two days.

Example 8

Validation of Expression Plasmids

Five to ten colonies of each of the four expression clones (BTB *E. coli* codon optimized gene version in pDOW1169 and pDAB1817 and BTB maize codon optimized gene versions in pDOW1169 and pDAB1817) were grown overnight and plasmid prepped from a 4 mL culture using the NucleoSpin Miniprep Kit™. Because pDOW1169 and pDAB1817 plasmids are low copy in number, the manufacturer's recommended protocol for isolation of low copy plasmids, P1 constructs or cosmids were followed. These plasmid preparations were then validated with restriction enzyme digestions using EcoRV, ApaL1/XhoI and NcoI/SacI.

Example 9

*Pseudomonas fluorescens* Test Expression Fermentation

Inoculation of Seed Flasks and Production Media Preparation

A single vial containing a 1 mL glycerol stock of the BTB expressing *Pseudomonas fluorescens* expression clones described above, was removed from the −80° C. freezer, quickly thawed (in hand) then gently inverted five times. One-hundred and fifty microliters (150 µL) of the glycerol stock was added to each of three, pre-sterilized, 250 mL bottom baffled flasks containing 50 mL of M9 salts+2% glucose for the pDOW1169 backbone and 50 mL LB+Tet (30 µg/mL) for the pDAB1817 backbone. Each flask was capped with a foam plug and incubated for 18.5 hours at 30° C. in an orbital shaker at 300 rpm with a one inch displacement.

Inoculation of Test Expression Flasks

The seed flasks were removed from the shaker and spectrophotometer readings (wavelength=OD600) were taken at a 1:10 dilution with water. Test expressions were done in triplicate for each clone. Only one seed flask was used to inoculate one shake flask. The shake flasks were inoculated with a 2% inoculum (4 mL) of seed flask culture and incubated for 24 hours at 30° C., at 300 rpm with a one inch displacement.

Induction of BTB Expression

Five milliliter (5 mL) samples were taken from each test expression flask and placed into 50 mL conical tubes and the pH was recorded. These samples were labeled as the "I0", or uninduced samples. A spectrophotometer reading at wavelength=OD600, using a 1:100 dilution with water was taken for the each flask. In addition, microscopic images were taken. Pre-induction samples of 0.5 mL from each flask were spun at 14K rpm in a table top centrifuge. The spent media was decanted and the pellet containing tube was placed at −20° C. Expression was induced by adding 60 µL of sterile 1M IPTG to each flask for a final concentration 0.3 mM. The flasks were incubated for up to 72 hours at 30° C., at 300 rpm with a one inch displacement. The sample isolation procedure described for the I0 samples was repeated for I24, I48, and I72 samples.

Example 10

DASGIP 1 L Fermentation

Seed Flask Preparation

The highest BTB expressing clone from the test expressions were the *Pseudomonas* strain which contained the construct consisting of a maize codon optimized version of the BTB gene within the pDAB1817 vector. This *Pseudomonas* strain was scaled up and was fermented in a 1 L DASGIP fermenter.

The cell growth conditions for the host cells described herein can include that which facilitates expression of the protein of interest, and/or that which facilitates fermentation of the expressed protein of interest. As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and mineral salts media; a rich medium may be used, but is preferably avoided. In another embodiment either a minimal medium or a mineral salts medium is selected. In still another embodiment, a minimal medium is selected. In yet another embodiment, a mineral salts medium is selected.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. The mineral salts medium does not have, but can include an organic nitrogen source, such as peptone, tryptone, amino acids, or a yeast extract. An inorganic nitrogen source can also be used and selected from among, e.g., ammonium salts, aqueous ammonia, and gaseous ammonia. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed below. The components can be added in the following order: first (NH4)HPO4, KH2PO4 and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose MgSO4 and thiamine-HCl can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for high cell density cultivation (HCDC) for growth of Pseudomonas species and related bacteria. The HCDC can start as a batch process which is followed by two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of Escherichia coli at controlled specific growth rate" J Biotechnol: 20(1) 17-27.

The expression system according to the present invention can be cultured in any fermentation format. For example, batch, fed-batch, semi-continuous, and continuous fermentation modes may be employed herein. Wherein the protein is excreted into the extracellular medium, continuous fermentation is preferred.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

In some embodiments, the expression system comprises a Pseudomonas host cell, e.g. Pseudomonas fluorescens. An advantage in using Pseudomonas fluorescens in expressing secreted proteins includes the ability of Pseudomonas fluorescens to be grown in high cell densities compared to E. coli or other bacterial expression systems. To this end, Pseudomonas fluorescens expressions systems according to the present invention can provide a cell density of about 20 g/L or more. The Pseudomonas fluorescens expressions systems according to the present invention can likewise provide a cell density of at least about 70 g/L, as stated in terms of biomass per volume, the biomass being measured as dry cell weight.

In one embodiment, the cell density will be at least about 20 g/L. In another embodiment, the cell density will be at least about 25 g/L, about 30 g/L, about 35 g/L, about 40 g/L, about 45 g/L, about 50 g/L, about 60 g/L, about 70 g/L, about 80 g/L, about 90 g/L., about 100 g/L, about 110 g/L, about 120 g/L, about 130 g/L, about 140 g/L, about or at least about 150 g/L.

In another embodiments, the cell density at induction will be between about 20 g/L and about 150 g/L; between about 20 g/L and about 120 g/L; about 20 g/L and about 80 g/L; about 25 g/L and about 80 g/L; about 30 g/L and about 80 g/L; about 35 g/L and about 80 g/L; about 40 g/L and about 80 g/L; about 45 g/L and about 80 g/L; about 50 g/L and about 80 g/L; about 50 g/L and about 75 g/L; about 50 g/L and about 70 g/L; about 40 g/L and about 80 g/L.

Analytical Gel Sample Preparation and Densitometry

The 0.5 mL samples from the I0, I24, I48 and I72 Pseudomonas fluorescens pellets prepared above were resuspended in Butterfield's™ phosphate buffer, sonicated (2×30 seconds with icing in between, Output 20, constant duty cycle) and clarified by centrifugation at maximum speed for 5 minutes in a table top microfuge tube centrifuge. The supernatant was transferred to a clean tube and the pellet resuspended in 0.5 mL phosphate buffer. Protein concentrations were determined using Protein Assay Dye Reagent™ (Bio-Rad).

Protein samples were prepared with 20.4 µg protein in a final volume of 51 µL including 4× reducing sample buffer and heated for 5 minutes at 100° C., prior to loading on the gel. A total of 6 ng total protein (15 µL of the heated gel loading sample prep) was loaded onto the analytical gels SDS-PAGE analysis was performed with Novex® 20 well, Tris-Glycine 4-20% (Invitrogen) run in 1× Novex® Tris-Glycine SDS running Buffer™ (Invitrogen). Gels were run at a constant 200V for 60 minutes, then stained with SimplyBlue™ SafeStain (Coomassie G-250; Invitrogen) and destained using MilliQ™ water according to the manufactures protocol. The 33.5 kDa band which comprises the BTB polypeptide migrates as a 40-50 kDa protein on this gel system.

Densitometry analysis to estimate expression levels was performed using a Typhoon Trio+ Imaging Scanner™ (GE Healthcare). The gels analysis used the 1D Gel Analysis component of the IMAGEQUANT™ software package (GE Healthcare). Densitometry analysis was done in manual (stepwise) mode. Background subtraction was "rolling ball" with a radius of 44, the standard molecular weight curve was fit using a cubic spline curve and the Standard BSA curve was calibrated using a quadratic equation. The expression level was estimated by dividing the amount of protein (in µg)

in the BTB band as determined by densitometry analysis by the volume (in μL) of protein sample added to the loading buffer, then multiplied by the dilution factor of 3.4× (51 μL sample volume/15 μL loaded onto gel).

Example 11

Results

The BTB protein that was *E. coli* codon optimized served as the starting point for shake flask expression tests. The *E. coli* codon biased BTB construct was cloned and inserted into two different expression vector/*Pseudomonas fluorescens* systems (e.g. pDOW1169 vector/*Pseudomonas* Pf10 strain or pDAB1817 vector/*Pseudomonas* MB214 strain) validated and expression tested. Each test expression was completed in triplicate. Table 2 summarizes BTB expression levels using the two different *Pseudomonas fluorescens* expression systems. The expression levels of these clones were very low with 0.011±0.009 g/L of BTB expressed for the pDOW1169 vector/*Pseudomonas* Pf10 strain culture and 0.021±0.025 g/L of BTB expressed for the pDAB1817 vector/MB214 *Pseudomonas* strain for a 72 hour induction. The BTB protein was expressed in the inclusion body fraction of the cell pellets for both *Pseudomonas* expression systems.

To increase the expression level of BTB, the gene was codon optimize to a maize preferred codon usage. The incorporation of the maize codons greatly increased BTB protein expression levels. The expression levels increased to 0.283±0.078 g/L for the pDOW1169 vector/*Pseudomonas* Pf10 strain cultures and 0.441±0.073 g/L pDAB1817 vector/MB214 *Pseudomonas* strain cultures for a 72 hour induction. These levels are 20 times the previously observed expression levels of the *E. coli* optimized polynucleotide sequence. The values recorded at the 72 hour induction levels were not significantly higher than the 48 hour induction levels of 0.229±0.100 g/L for the pDOW1169 vector/*Pseudomonas* Pf10 strain and 0.410±0.059 g/L pDAB1817 vector/MB214 *Pseudomonas* strain. The BTB protein was expressed in the inclusion body fraction of the cell pellets for both *Pseudomonas* expression systems.

TABLE 2

Expression results of BTB protein expressed in the inclusion body fraction.

| Codon Bias | Pf10 (pDOW1169 backbone; Uracil auxotroph) | MB214 (pDAB1817 backbone; tetR) | Fermentation Type |
|---|---|---|---|
| *E. coli* | 0.011 ± 0.009 g/L | 0.021 ± 0.025 g/L | Shake flask |
| maize | 0.283 ± 0.078 g/L | 0.441 ± 0.073 g/L | Shake flask |
| maize | Not Determined | 0.84 g/L | DASGIP |

As determined by test expressions analysis, the maize codon optimized BTB clone in pDAB1817 vector/MB214 *Pseudomonas* strain was the best expresser and therefore grown in two separate DASGIP fermenters. To test pH effects on BTB expression the pH at induction was maintained at 6.0 in one experiment and 6.5 in a second experiment. Fermentation was carried out for 48 hours post induction, not 72, because the expression levels were not appreciably higher at 172 in shake flasks and expression progresses faster in the controlled conditions of fermenters. The observed expression level in the fermenter with pH maintained at 6.0 was 0.83 g/L and 0.84 g/L in the fermenter with a pH maintained at 6.5. The pH of the culture had no discernable effect on BTB expression levels. The protein production was almost twice using the DASGIP fermenters as compared to the shake flask expression protein levels, and nearly 40 times the level of the *E. coli* codon biased sequence.

What is claimed is:

1. A method for codon optimizing a polynucleotide for the expression of a protein in a bacterial host cell, the method comprising replacing at least one codon in the polynucleotide with a codon that is used more frequently in the genes of a plant than in the genes of the bacterial host cell, such that
   GC and TA doublets are removed from the polynucleotide sequence;
   predicted ribonucleic acid (RNA) stem-loop-forming structures are removed from the polynucleotide sequence;
   at least one restriction enzyme binding sequence is removed from the polynucleotide sequence;
   sequence blocks that have more than about six consecutive residues of [G+C] or [A+T] are removed from the polynucleotide sequence; and
   exon:intron junctions, poly-A addition signals, and RNA polymerase termination signals are removed from the polynucleotide sequence.

2. A bacterial host cell comprising the polynucleotide produced by the method according to claim 1.

3. The bacterial host cell of claim 2, wherein the bacterial host cell is a *Pseudomonas* host cell, and *Escherichia* host cell, an *Acidovorax* host cell, and *Brevundimonas* host cell, an *Burkholderia* host cell, an *Hydrogenophaga* host cell, an *Oceanimonas* host cell, an *Ralstonia* host cell, an *Stenotrophomonas* host cell, an *Sphingomonas* host cell, an *Xanthomonas* host cell, or an *Acidomonas* host cell.

4. The method according to claim 1, wherein the at least one codon is replaced with a codon that is used more frequently in the genes of a monocotyledonous plant than in the genes of the bacterial host cell, or the at least one codon is replaced with a codon that is used more frequently in the genes of a dicotyledonous plant than in the genes of the bacterial host cell.

5. The method according to claim 1, wherein the at least one codon is replaced with a codon that is used more frequently in the genes of *Zea mays* than in the genes of the bacterial host cell.

6. The method according to claim 1, wherein the bacterial host cell is a *Pseudomonas* host cell, and *Escherichia* host cell, an *Acidovorax* host cell, and *Brevundimonas* host cell, an *Burkholderia* host cell, an *Hydrogenophaga* host cell, an *Oceanimonas* host cell, an *Ralstonia* host cell, an *Stenotrophomonas* host cell, an *Sphingomonas* host cell, an *Xanthomonas* host cell, or an *Acidomonas* host cell.

7. The method according to claim 1, wherein the bacterial host cell is a *Pseudomonas fluorescens* host cell.

8. The method according to claim 5, wherein the bacterial host cell is a *Pseudomonas fluorescens* host cell.

9. A method for codon optimizing a polynucleotide encoding a protein for the expression of the protein in a bacterial host cell, the method comprising replacing at least one codon in the polynucleotide with a codon that is used more frequently in the genes of a plant than in the genes of the bacterial host cell.

10. The method according to claim 9, wherein the at least one codon is replaced with a codon that is used more frequently in the genes of *Zea mays* than in the genes of the bacterial host cell.

11. The method according to claim 9, wherein the bacterial host cell is a *Pseudomonas fluorescens* host cell.

12. The method according to claim 10, wherein the bacterial host cell is a *Pseudomonas fluorescens* host cell.

* * * * *